United States Patent
Hampton

(10) Patent No.: US 6,875,418 B2
(45) Date of Patent: Apr. 5, 2005

(54) METHOD OF EARLY DETECTION OF DUCHENNE MUSCULAR DYSTROPHY AND OTHER NEUROMUSCULAR DISEASE

(75) Inventor: Thomas G. Hampton, Framingham, MA (US)

(73) Assignee: Mouse Specifics, Inc., Boston, MA (US)

( * ) Notice: Subject to any disclaimer, the term of this patent is extended or adjusted under 35 U.S.C. 154(b) by 35 days.

(21) Appl. No.: 10/175,691

(22) Filed: Jun. 19, 2002

(65) Prior Publication Data

US 2003/0003052 A1 Jan. 2, 2003

Related U.S. Application Data

(60) Provisional application No. 60/299,302, filed on Jun. 19, 2001, and provisional application No. 60/338,821, filed on Nov. 17, 2001.

(51) Int. Cl.[7] .............. A61K 49/00; A61B 5/00
(52) U.S. Cl. ............... 424/9.1; 600/300; 600/301
(58) Field of Search .................. 424/9.1; 600/300, 600/301

(56) References Cited

U.S. PATENT DOCUMENTS

| 4,794,934 A | | 1/1989 | Motoyama et al. | 128/734 |
| 5,434,142 A | | 7/1995 | Antoku et al. | 514/53 |
| 5,704,369 A | * | 1/1998 | Scinto et al. | 600/558 |
| 5,778,893 A | | 7/1998 | Potter | |

OTHER PUBLICATIONS

Kenuen et al. Medline Abstract, AN 87322041, 1987.*

* cited by examiner

Primary Examiner—Shengjun Wang
(74) Attorney, Agent, or Firm—Lahive & Cockfield, LLP

(57) ABSTRACT

The mdx mouse is a model of Duchenne muscular dystrophy. The present invention describes that mdx mice exhibited clinically relevant cardiac phenotypes. A non-invasive method of recording electrocardiograms (ECGs) was used to a study mdx mice (n=15) and control mice (n=15). The mdx mice had significant tachycardia, consistent with observations in patients with muscular dystrophy. Heart-rate was nearly 15% faster in mdx mice than control mice (P<0.01). ECGs revealed significant shortening of the rate-corrected QT interval duration (QTc) in mdx mice compared to control mice (P<0.05). PR interval duration were shorter at baseline in mdx compared to control mice (P<0.05). The muscarinic antagonist atropine significantly increased heart-rate and decreased PR interval duration in C57 mice. Paradoxically, atropine significantly decreased heart-rate and increased PR interval duration in all mdx mice. Pharmacological autonomic blockade and baroreflex sensitivity testing demonstrated an imbalance in autonomic nervous system modulation of heart-rate, with decreased parasympathetic activity and increased sympathetic activity in mdx mice. These electrocardiographic findings in dystrophin-deficient mice provide new bases for diagnosing, understanding, and treating patients with Duchenne muscular dystrophy.

18 Claims, 8 Drawing Sheets

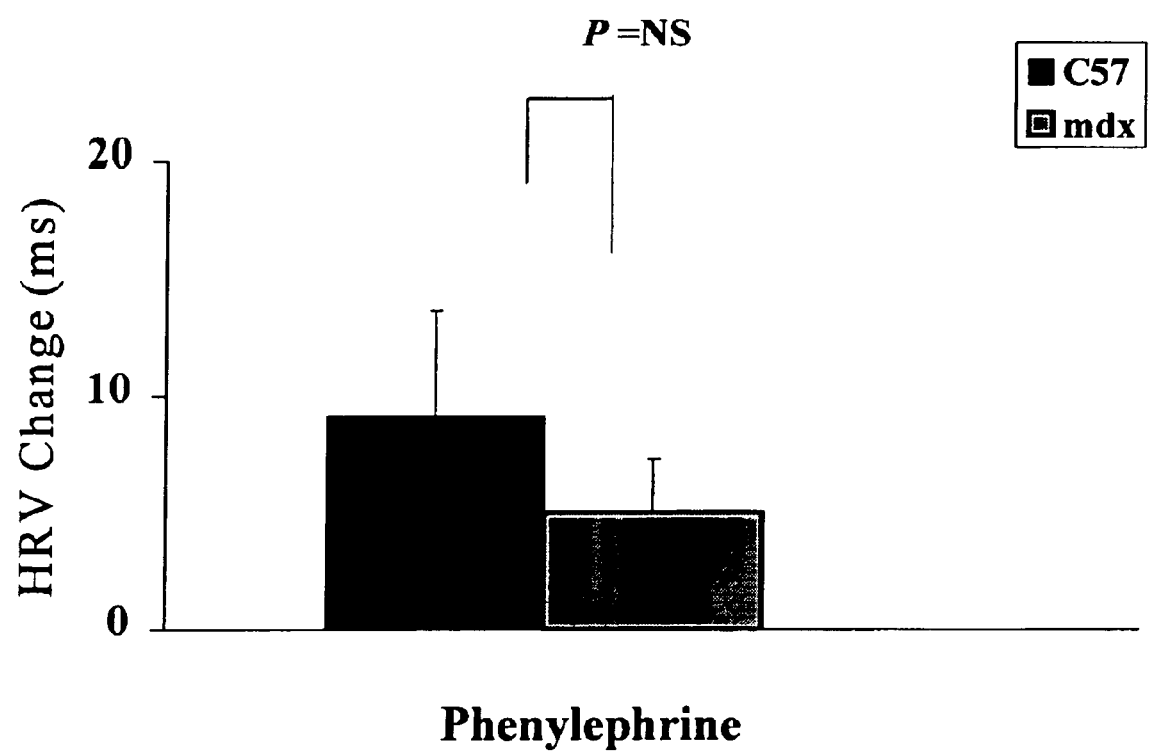

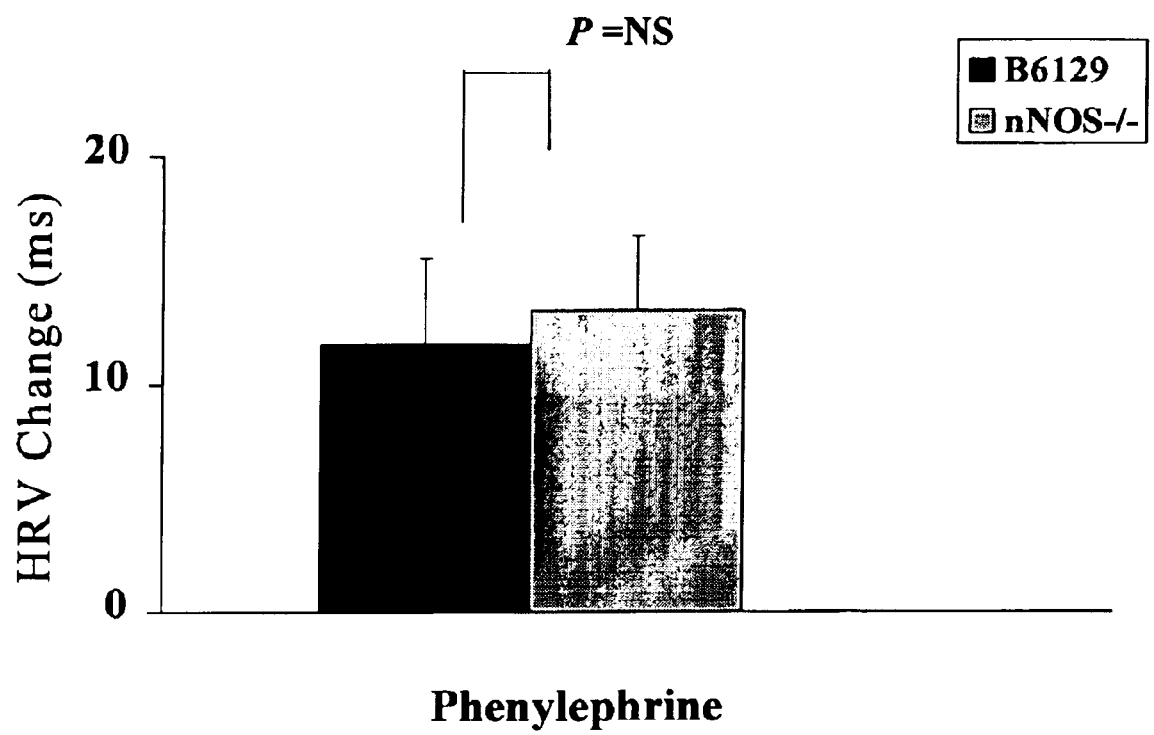

METHOD OF EARLY DETECTION OF DUCHENNE MUSCULAR DYSTROPHY AND OTHER NEUROMUSCULAR DISEASE

RELATED APPLICATIONS

This application claims priority to U.S. provisional patent application Ser. No. 60/299,302, filed Jun. 19, 2001, and to U.S. provisional patent application Ser. No. 60/338,821, filed Nov. 17, 2001. The contents of these provisional patent applications are incorporated herein by reference in their entirety.

BACKGROUND OF THE INVENTION

Dysfunction of the autonomic nervous system is an under-recognized but important aspect of the etiological and clinical manifestation of neuromuscular disorder such as Duchenne muscular dystrophy (DMD). DMD is an X-linked inherited disorder that affects over nearly 30 out of every 100,000 boys born in the United States. The disorder results from a defect in the gene for an enormous protein called dystrophin, which forms part of the scaffold in muscle fibers. Although the disorder is present from the initial stages of fetal development, there is no physical indication at birth that the baby is abnormal. Rarely is there physical diagnosis in the first year of life. Problems are usually not evident until 18 months to 4 years of age. Usually diagnosis is not made until the child is five. Nearly 50% of affected boys do not walk until 18 months of age or later. Duchenne children have difficulty climbing and getting up from the floor. Parents often comment that their child falls frequently. By the age 3 to 5 years, generalized muscle weakness becomes more obvious. Parents may be falsely encouraged by a seeming improvement at school age, but this may be due to natural growth and development. Weakness progresses rapidly after age 8 or 9, resulting in the inability to walk or stand unassisted. Leg braces may make walking possible for a year or two, but by early adolescence walking becomes impossible. There are some boys with Duchenne muscular dystrophy who have problems with delay in mental or language development. Eventually all the major muscles are affected. Lung capacity may decrease, resulting in an increased susceptibility to respiratory infections. Cardiac and respiratory failure are common in Duchenne patients.

Autonomic nervous system abnormalities have now been frequently reported in patients. The cardiac phenotype includes decreased parasympathetic nervous activity and increased sympathetic nervous activity. Currently there is no reliable mode of prenatal diagnosis or cure. For a series of reasons, diagnosis of Duchenne patients using DNA markers from amniocytes is error ridden and deletion mutants are detectable in only 65% of cases. Therefore, early detection of the disease before locomotor or autonomic disturbances reduce quality of life or irreversibly affect outcome of the disease could significantly improve life-quality prospects and longevity in those afflicted with dystrophin-deficiency related diseases.

SUMMARY OF THE INVENTION

The present invention provides method of diagnosing or aiding in diagnosing of a perturbation of an autonomic nervous system in a subject. Using the methods for non-invasively recording electrocardiograms (ECGs) to study a subject suffering from or at a risk from suffering from an autonomic nervous system disorder and compare it with a response under similar conditions in a normal subject.

In one embodiment, the method comprises the steps of: a) administering, into a body of the subject, an effective amount of a cholinergic agent or a derivative thereof; and, b) determining whether the cholinergic agent or a derivative thereof, elicits a cholinomimetic effect in the subject, as opposed to a cholinergic effect, thereby identifying whether the subject has indications of the perturbation of the autonomic nervous system.

In one aspect, the perturbation of the autonomic nervous system is determined by detecting a change in heart-rate of the subject in response to the cholinergic agent or a derivative thereof.

In one embodiment, the change in heart rate is measured as a decrease in heart rate activity.

In another embodiment, the change in heart rate is measured as an increase in heart rate activity.

In one embodiment, the change in the heart rate is determined using a detector supplying data associated with electrocardiogram signals and providing an electrocardiogram using an apparatus for interpreting the data associated with electrocardiogram signals of the subject.

In one aspect, the changes in heart rate activity are detected by a computing apparatus.

In another aspect, the computing apparatus further comprises a digital processor, a working memory, and a database, which records changes in heart rate in the subject.

In one embodiment, the perturbation is caused by an alteration in property and function of an acetylcholine receptor.

In another embodiment, the perturbation is caused by an alteration in property and function of a cholinergic receptor.

In yet another embodiment, the cholinergic receptor is a muscarinic receptor.

In a further embodiment, the perturbation is caused by a perturbation in acetylcholine concentration.

In one aspect, the perturbation is caused by perturbation in acetylcholinesterase concentration.

In another aspect, the perturbation is caused by a deficiency in dystrophin or by alteration in dystrophin associated protein.

In one embodiment, the perturbation of the autonomous nervous system results in a disorder or that the autonomous nervous system is substantially affected by other disorders including other infectious diseases (e.g., tetanus, diphtheria), and immunologic diseases (e.g., acquired immunodeficiency syndrome). Disorders of central autonomic control also contribute substantially to a wide variety of autonomous nervous system disorder.

In another embodiment, the disorder is selected from a group consisting of: peripheral nervous system disorder, a neuromuscular disorder, a neurodegenerative disorder, a cardiovascular disorder, a lateral sclerosis, a diabetic neuropathy, an arteriosclerosis, a tachycardia, a bradycardia, a pressure overload, a hypertension, an atrial fibrillation, an atrial flutter, a dilated cardiomyopathy, an idiopathic cardiomyopathy, a myocardial infarction, a coronary artery disorder, a coronary artery spasm, and an arrhythmia.

In one aspect, the cholinergic agent or a derivative thereof, is a muscarinic agent.

In another aspect, the muscarinic agent is a muscarinic antagonist or a derivative thereof.

In yet another aspect, the muscarinic antagonist is selected from a group consisting of; an atropine, a scopolamine, a propantheline, a pirezapine, and a derivative thereof.

In one embodiment, the agent is administered intravenously, intraperitonially, ophthalmologically, buccal, intracoronary, intramuscularly, topically, intranasally, rectally, sublingually, orally, subcutaneously, by patch, or inhalation.

In one aspect, the subject is a human.

In another aspect, the subject further comprises of one or more of age, sex, and ethnic origin.

In one embodiment the invention pertains to a method of diagnosing or aiding in diagnosing of Duchenne muscular dystrophy in a subject, the method comprising the steps of: a) administering, into a body of the subject, an effective amount of a cholinergic agent or a derivative thereof; and, b) determining whether the cholinergic agent or a derivative thereof, elicits a cholinomimetic effect in the subject, as opposed to a cholinergic effect.

In one aspect, the cholinergic agent or a derivative thereof, elicits a change in heart rate.

In another aspect, the change in the heart rate decreases the heart rate of the subject in response to the cholinergic agent or a derivative thereof, thereby indicative of Duchenne muscular dystrophy in the subject.

In one embodiment, the present invention provides a method for treating a heart-disorder state associated with dystrophin or dystrophin-associated protein in a subject in need thereof, the method comprising the step of administering to the subject a therapeutically effective amount of one of a cholinergic agent, a muscarinic agent, an adrenergic agent, and a derivative thereof, such that treatment of heart-disorder state occurs.

In one aspect, the agent is administered intravenously, intraperitonially, ophthalmologically, buccal, intracoronary, intramuscularly, topically, intranasally, rectally, sublingually, orally, subcutaneously, by patch, or inhalation.

In another aspect, a second effective amount of one of the cholinergic, the muscarinic agent, and a derivative thereof, is administered about one, two or three times in a day after administration of a first effective amount of one of a cholinergic agent, a muscarinic agent, an adrenergic agent, and a derivative thereof.

In still another aspect, one or more further effective amounts of one of the cholinergic agent, the muscarinic agent, the adrenergic agent, and a derivative thereof, is added at intervals of one day or more.

In one aspect, the present invention pertains to a method of diagnosing or aiding in diagnosing a subject suffering from a dystrophin-deficient disorder, or at risk of developing a dystrophin-deficient disorder comprising the steps of: a) administering topically into an eye of the subject an effective amount of one of a cholinergic, a muscarinic agent, and a derivative thereof, to induce a physiological change in the eye; b) comparing a physiological change in the subject with a response under similar conditions in a normal subject, thereby identifying whether the subject suffers from dystrophin-deficient disorder.

In one embodiment, the physiological response is determined by a change in pupil diameter in the eye.

BRIEF DESCRIPTION OF FIGURES

The aforementioned features, and other features and aspects of the present invention, will become better understood with regard to the following description and accompanying figures, wherein:

FIG. 3b shows HRV response to phenylephrine. HRV after phenylephrine administration remained significantly smaller in mdx mice compared to C57 mice (8.5±2.5 ms vs. 28.6±4.1 ms P<0.05).

FIG. 4b shows HRV response to phenylephrine. Phenylephrine administration resulted in an equivalent increase in HRV in nNOS -/- (+35±6 bpm) and B6129 mice (+18±8 bpm) (P=NS).

DEFINITIONS

Figure 1:
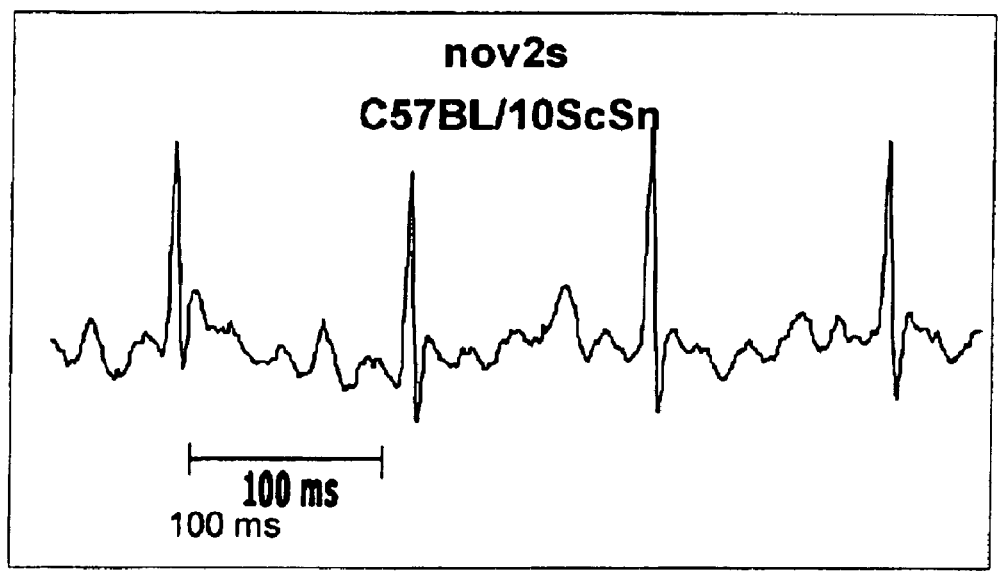
FIG. 1 shows electrocardiograms from a conscious male C57 control mouse (top) and a male mdx mouse (bottom). Heart-rate was significantly faster in mdx mice than in C57 control mice at baseline. In the control mouse with the ECG signal shown, HR=595 bpm, QRS=9.6 ms, and QT=75.0 ms. In the mdx mouse shown, HR=814 bpm, QRS=7.5 ms, and QT=49.6 ms.
Figure 1:
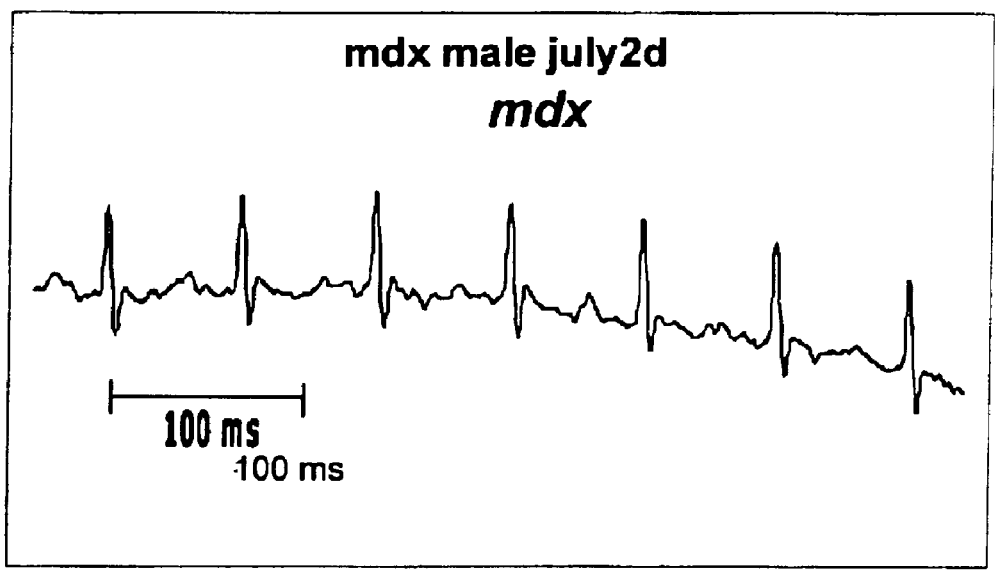

In order to avoid ambiguity in terminology as well as to provide a clear and precise understanding of the scope of the present methodology, a set of specific terms and explicit definitions are given below. These words and their meanings will be employed repeatedly and routinely in this disclosure and the stated definitions are to be accepted as written and as part of the general lexicon and vocabulary in this art.

As used herein, the term "perturbation" (or the act of perturbing, or the state of being perturbed) refers to a disturbance of state of equilibrium of any of the enzymes (e.g., acetylcholinesterase), hormones, proteins, receptors (e.g., acetylcholine receptor) or any other biological component of the signaling pathway or the cellular mechanism which directly or indirectly affects the function of the autonomic nervous system. The responses of an autonomic nervous system to an application of an endogenous or exogenous agent (e.g., a drug) are also encompassed by this definition, wherein an "endogenous agent" refers to a compound or composition developing or originating within the person or arising from causes within the person's body, and an "exogenous agent" refers to a compound or composition synthesized, found, or originating outside the person's body.

As used herein, the term "cholinergic" refers to term pertaining to the neural transmitter acetylcholine. The term is particularly used to designate nerve fibers that release acetylcholine at their terminals, or the physiological effects produced by the stimulation of these nerve fibers, or the acetylcholine receptors on the post synaptic membrane, or chemical agents and drugs that imitate the effects of-acetylcholine. "Cholinergic" also refers to cholinergic agent resembling acetylcholine in pharmacological action, stimulated by or releasing acetylcholine or a related compound. Whereas, a "cholinergic agent" refers to an agent that mimics the action of the parasympathetic nervous system (e.g., cholinergic drugs). A "cholinergic antagonists" refers to an agent that binds to but do not activate cholinergic receptor, thereby blocking the actions of acetylcholine or cholinergic agonists. A "cholinergic agonist" refers to an agent that binds to and activates a cholinergic receptor.

As used herein, the term "cholinomimetic" refers to having an action similar to that of acetylcholine, the substance liberated by cholinergic nerves.

As used herein, the term "autonomic nervous system" refers to neurons that are not under conscious control, comprising two antagonistic components, the sympathetic and parasympathetic nervous systems. The autonomic nervous system regulates key functions including the activity of the cardiac (heart) muscle, smooth muscles (e.g., of the gut), and glands. The autonomic nervous system has two divisions:

1. The sympathetic nervous system that accelerates the heart-rate, constricts blood vessels, and raises blood pressure.

2. The parasympathetic nervous system slows the heart-rate, increases intestinal and gland activity, and relaxes sphincter muscles.

As used herein, the term "autonomic nervous system disorder or disease" refers to diseases that have their major effects on the autonomic nervous system. The autonomic nervous system disorder or disease includes, but is not limited to, a peripheral nervous system disorder, a neuromuscular disorder; a neurodegenerative disorder, a cardiovascular disorder, a lateral sclerosis, a diabetic neuropathy, an arteriosclerosis, a tachycardia, a bradycardia, a pressure overload, a hypertension, an atrial fibrillation, an atrial flutter, a dilated cardiomyopathy, an idiopathic cardiomyopathy, a myocardial infarction, a coronary artery disorder, a coronary artery spasm, or an arrhythmia. The autonomic nervous system may be seriously affected in many other disorders including other infectious diseases (e.g., tetanus, diphtheria), and immunologic diseases (e.g., acquired immunodeficiency syndrome). Disorders of central autonomic control also contribute substantially to a wide variety of problems (e.g., eating disorders, panic disorder, water-electrolyte imbalance, cardiovascular diseases).

As used herein, the term "heart-rate" refers to a complete cardiac cycle, including spread of the electrical impulse and the consequent mechanical contraction, Whereas the term "cardiac cycle" refers to the complete round of cardiac systole and diastole with the intervals between, or commencing with, any event in the heart's action to the moment when that same event is repeated.

As used herein, the term "adrenergic" refers to designating activation by, characteristic of, or a secreting of the neural transmitter epinephrine or substances with similar epinephrine-like activity. The term is also used to refer to those postganglionic sympathetic nerve fibers that liberate norepinephrine in response to a nerve impulse; and is typically used to identify an agent that produces such an effect. The term "adrenergic agent" as used herein refers to drugs that act on adrenergic receptors or affect the life cycle of adrenergic transmitters. Included here are adrenergic agonists (e.g., phenylephrine) and antagonists (e.g., propranolol) and agents that affect the synthesis, storage, uptake, metabolism, or release of adrenergic transmitters.

As used herein, the term "neural transmitter" (also Neurotransmitter and Synaptic Transmitter) refers to an agent or a compound or substance that serves to transmit a nerve impulse between cells at a synapse or a neuromuscular junction. Such compounds include but are not limited to acetylcholine, epinephrine, norepinephrine, dopamine, serotonin, γ-aminobutyric acid, glycine, and glutamate.

An "agent" or a "compound" as used herein interchangeably refers to any chemical or biological material or substance whose effects (e.g change in heart-rate or change in heart-rate variability) can be evaluated using a subject and methods of the present invention. Such chemicals or biological materials or substances include, but are not limited to, organic molecules including pharmaceutically acceptable molecules, hormones, polypeptides, peptides, polynucleotides, and polynucleotide analogs or the derivatives thereof. Many organizations (e.g., the National Institutes of Health, pharmaceutical and chemical corporations) have large libraries of chemical or biological compounds from natural or synthetic processes, or fermentation broths or extracts.

As used herein, the term "agonist" refers to a compound or substance that imitates, mimics, or acts in a manner similar to the activity or function of a specified tissue, composition or agent or derivatives thereof.

As used herein, the term "antagonist" refers to a substance that blocks the activity or function of a specified tissue, composition or agent or derivatives thereof.

As used herein, the term "mediator" refers to a compound, composition, agent or substance or derivatives thereof that influences, effects, intervenes, contradicts, mitigates, modifies, promotes, or is involved with an activity or function in a specified manner.

The terms "subject," "individual" or "patient" are used interchangeably herein and refer to a vertebrate, preferably a mammal. Mammals include, but are not limited to, murines, simians, humans, farm animals, sport animals and pets.

An "effective amount" is an amount sufficient to effect beneficial or desired biological results. An effective amount can be administered in one or more administrations, applications or dosages.

As used herein, the term "heart-rate variability" includes a high-frequency (HF) component and a low-frequency (LF) component. The HF component is synchronous to the breath. The LF component is presumed to be relative to blood vessel movement or pressoreceptor reflex. The low-frequency component can be further divided into a very-low-frequency (VLF) component and LF component.

DETAILED DESCRIPTION

The present invention is directed to non-invasive methods for diagnosing autonomous nervous system disorder in a living human subject. As will be described in detail below, these diagnostic methods take advantage of a new recognition that some aspects of the typical Duchenne muscular dystrophy (DMD) subject's autonomic nervous system are hypersensitive to neural transmitter mediators, such as cholinergic agents. In one method, measurements are made of changes in heart rate in response to neural transmitter mediators (cholinergic antagonists) when such mediators are applied at concentrations known to elicit a cholinergic effect, but to the contrary, elicits a cholinomimetic effect in individuals suffering from or who are at risk of suffering from disorders that may result in unbalanced autonomic nervous system control, such as, Duchenne muscular dystrophy.

In alternative method, measurements are made of changes in pupil diameter in response to neural transmitter mediators when such mediators are applied at concentrations known to be too low to significantly affect pupil diameter in normal subjects, whereas in subjects suffering from or who are at risk of suffering from a disorder that may result in unbalanced autonomic nervous system control, such as, Duchenne muscular dystrophy, a change in pupil diameter occurs.

The present invention also provides methods for treating a subject suffering from an autonomic nervous system disorder or disorders, such as, Duchenne muscular dystrophy that results in an imbalanced autonomic nervous system disorder. In particular, the method includes administering to a subject suffering from autonomic nervous system disorder or who at risk of suffering from such a disorder an amount of an agent effective for providing some degree of diagnosis of the progression of the perturbation in the autonomic nervous system which results in a disorder (i.e., provide diagnostic effects), amelioration of the symptoms of the perturbation of the autonomic nervous system and the related disorder (e.g., neuromuscular disorder), and amelioration of the reoccurrence of the autonomic nervous system disorder. The method involves administering an effective amount of an agent selected from the cholinergic antagonists or agonist or the derivatives thereof. The agents can be employed in a free base form or in a salt form (e.g., as pharmaceutically acceptable salts, such as chloride, perchlorate, ascorbate, sulfate, tartrate, fumarate, citrate, malate, lactate or aspartate salts). Autonomic nervous system perturbation and resulting disorders can be diagnosed in accordance with the present invention, which include diagnoses of perturbations of the autonomic nervous system concomitant with or contributing to any disease (e.g. neuromuscular disorder, amyotrophic lateral sclerosis, diabetic neuropathy, or DMD) in which the properties and functions of muscarinic receptors may be altered such that cholinomimetic effects of cholinergic agents are realized when the cholinergic antagonistic effects of the agents are anticipated.

The present diagnostic methods are relatively noninvasive. The methodology utilizes automated equipment, which can repetitively measure heart-rate changes over time, and cumulatively record such data as it is obtained or which can accurately monitor heart-rate in response to stimulation (e.g., cholinergic or adrenergic antagonist or agonist). The data so obtained can then be mathematically analyzed to provide a quantitative clinical result for comparison with an established numerical standard range of normal and abnormal values. In this manner, a definite, unambiguous, and reliable determination can be made as to whether or not that living human subject is afflicted with a disease related to perturbation in the autonomic nervous system (e.g., neuromuscular disorder).

The use of automated equipment to monitor and record changes in heart-rate responses provides a large quantum of empirical data, which can be used, for making a clinical diagnosis. The automated equipment is able to observe and measure heart-rate and changes in heart-rate, accurately, and repetitively.

The diagnostic methodology as a whole makes minimal demands upon the patient; does not involve physical exercise or fatiguing manipulations; and avoids the use of systemic medication. Instead, the methods of the present invention rely upon the use of dilute concentrations of neural transmitter mediators such as cholinergic antagonists and agonists and adrenergic antagonists and agonists. These neural transmitter mediators are administered to subjects suffering from autonomic nervous system disorder or who at risk of suffering from such a disorder at concentrations, which doe not adversely affect the heart or substantially influence pupillary responses in normal individuals. Accordingly, there is little or no probability that the diagnostic examination process will cause undesirable side effects.

The diagnostic methods may be performed relatively easily and can be completed within about an hour. The diagnostic data are then generated as quickly as the central processing unit of the automated apparatus can operate; and the results appear in printed form or in visual form on a monitor and/or may be transferred to a remote reference facility for final analysis as is most desired or required under the use circumstances.

The diagnostic methods employ a pharmacological manipulation of heart-rate. In one preferred method, a neurotransmitter mediator (cholinergic or adrenergic antagonist or agonist) is introduced in an individual being tested and his change in heart-rate (percent change over baseline or rate of change) is compared to norms established for a population of, preferably, age-matched, normal individuals. A significant difference from the established norm in the heart-rate response of such an individual serves to diagnose disorders that may result in unbalanced autonomic nervous system control (e.g., DMD).

In accordance with one embodiment, an agent (e.g., cholinergic antagonist) is applied to a subject's eye and the constriction of his pupil in response to the agent (e.g., cholinergic antagonist) is compared to the constriction of normal individuals. Again, it is preferred that subjects be compared to an age matched normal population. A significant difference in constriction diameter would be indicative of DMD. An alternative method uses one eye of the individual as the targeted eye for treatment with neural mediators while the other eye is employed as an untreated control. In this manner, the difference in pupillary response is thus measured between the two eyes of the same living subject.

The diagnostic methodology can be performed and practiced in several different modes. These procedures include measuring a change in heart-rate or heart rate variability; a change in pupil diameter dilation; pupil diameter constriction, and the rate of pupil diameter changes.

The present invention is thus based on the surprising and unexpected findings, as detailed herein below, that it is possible to administer a cholinergic agent (e.g., atropine) and measure the physiological response, such as heart-rate, to provide an indication of perturbation in the autonomic nervous system (e.g., neuromuscular disorder). For example, when the administration of the appropriate dose of atropine or similar agent increases heart-rate or does not change heart-rate significantly in a subject, the response is considered normal or healthy. However, if administration of the same or comparable dose of atropine or similar agent significantly decreases heart-rate in a subject, the response is considered abnormal, or indicative of an abnormality that may be associated with a perturbation in the autonomic nervous system. In a preferred embodiment, when the heart-rate after a dose of atropine administration significantly increases heart-rate or does not significantly change heart-rate in healthy subjects (e.g., infants or young children), the same dose may significantly decrease heart-rate in babies that have undiagnosed autonomic nervous system disorder (e.g., neuromuscular disorder, such as Duchenne muscular dystrophy).

In accordance with one embodiment, the cholinomimetic effect of atropine in a subject deficient in dystrophin (e.g., a reduction in heart-rate after atropine administration) is compared to the observed and expected muscarinic antagonist effect in control subject to the same concentration of atropine administered (e.g., either no change or an increase in heart-rate after atropine administration). Based on these observations, a new method is provided for detecting dystrophin-deficiency (e.g., diagnosis of Duchenne muscular dystrophy) based on the physiological response (e.g. heart-rate changes) after administration of a muscarinic agent (e.g. atropine).

The present invention also relates to diagnoses of perturbations of the autonomic nervous system concomitant with or contributing to any disease (e.g., amyotrophic lateral sclerosis, or diabetic neuropathy) in which the properties and functions of muscarinic receptors may be altered such that cholinomimetic effects of cholinergic agents are realized when the muscarinic antagonistic effects of the agents are anticipated. For example, as described above, atropine administered to a subject (e.g., infants or individuals) who may be deficient in dystrophin will cause heart-rate to decrease. The anticipated effect, increase in heart-rate, is realized in control subject; the opposite effect, decrease in heart-rate, is realized in the dystrophin-deficient subject. Thus in a subject, deficient in dystrophin, administration of this test reveals which subject is deficient in dystrophin, based on this contrary observation. As shown in the examples, at baseline, heart-rate in dystrophin-deficient mice is elevated above that of control mice (~15%). Mancinelli et al. (1989) *Proc R Soc Lond B Biol Sci* 237; 257–54, showed that the average frequency of openings of acetylcholine receptors is about 4 times higher in tissue from dystrophin-deficient patients than in control. The examples in this study show that the more frequent openings are related to the ~15% increase in heart-rate in dystrophin-deficient mice and patients at baseline. Atropine potentiates acetylcholine at certain small dosages, therefore, the conditions of dystrophin-deficiency are such that atropine potentiates acetylcholine at larger doses, dosages at which in control settings have an antagonistic effect. Moreover, since atropine can act as an anticholinesterase inhibitor at certain concentrations, in the setting of dystrophin-deficiency, the effect of atropine can be as an anticholinesterase inhibitor, thus further potentiating the effects of acetylcholine. Thus, the innovation is to use a muscarinic antagonist that operates as a cholinomimetic in disease settings as a diagnostic tool acutely and as a therapy prospectively. The change Dystrophin deficient subjects of the present invention include subjects, who lack or have reduced, mutated, or dysfunctional expression of dystrophin gene or the protein encoded by this gene. The subjects could further lack or have reduced, mutated, or dysfunctional expression of proteins that associate with dystrophin. Dystrophin is associated with a large oligomeric complex of sarcolemmal proteins and glycoproteins, the dystrophin-glycoprotein complex (DGC). The components of the DGC include several proteins on the cytoplasmic side (e.g. dystrophin, the syntrophins and dystrobrevin) and two transmembrane glyco-protein sub-complexes (the dystroglycans and sarcoglycans). The DGC primarily comprises of but is not limited to: glycoprotein complex (e.g., dystroglycan or sarcoglycan complex), cytoplasmic complex (e.g., syntrophin complex) and proteins in other complexes (e.g., dystrobrevin, sarcospan, caveolin, and related proteins). Thus in one embodiment, the present invention encompasses all subjects who are suffering from or at risk of suffering from a muscular dystrophy (e.g., Duchenne muscular dystrophy) as a result of malfunction in dystrophin or any of the proteins that directly (e.g., via protein-protein interaction) or indirectly (e.g., via adapter or chaperon molecules) associate with dystrophin (i.e., dystrophin associated proteins).

In accordance with another embodiment, the present invention provides a method of corrective treatment for dystrophin-deficient patients. For example, in dystrophin-deficient subject, the alpha-agonist phenylephrine reduces heart-rate in the direction of normal and increases heart-rate variability in the direction of normal. Yet, the changes are not as dramatic as in controls, indicating that the correct dose will most likely be a corrective treatment for dystrophin-deficient patients. Thus in a one embodiment, the present invention provides a method for treatment of, or preventative agent against, the tachycardia and abnormal autonomic control of heart rhythm in dystrophin-deficient subjects, phenylephrine or other alpha-adrenoceptor agonists aimed at increasing parasympathetic modulation of heart rhythm.

Furthermore, the present invention provides methods for diagnosing and treating either autonomic nervous disorders that cause the cardiac disorders or for the cardiac disorders concomitant with diseases affecting the autonomic nervous system, and in particular reflect a depression of parasympathetic modulation of heart rhythm, agents that increase parasympathetic nervous control of heart rhythm. The present invention further describes a method for treatment, or preventative agent against the tachycardia and abnormal autonomic control of heart rhythm in dystrophin-deficient subjects, cholinergic agents and dosages of those cholinergic agents that, in healthy subjects would act as muscarinic antagonists, function in dystrophin-deficient subjects as cholinomimetic agents, resulting in a reduction in the elevated heart-rate in dystrophin-deficient subjects that could otherwise result in eventual cardiac failure if not maintained at normal healthy levels.

The present invention also describes a method of treatment for or a preventative agent against the tachycardia and/or abnormal autonomic control of heart rhythm in diseases which perturb the muscarinic receptors such that muscarinic antagonists actually effect cholinergic properties, cholinergic agents and dosages of those cholinergic agents that, in healthy subjects would act as muscarinic antagonists, function in these disease conditions as cholinomimetic agents, resulting in a reduction in the elevated heart-rate and correction of autonomic dysfunctional control of heart rhythm in diseased subjects that could otherwise result in eventual cardiac failure if not maintained at normal healthy levels.

Atropine is one such muscarinic agent that may be cardioprotective in Duchenne muscular dystrophy, a disease that so perturbs the muscarinic receptors, by causing heart-rate to decrease rather than to increase, the contrary effect as to what is observed in healthy individuals. Therefore, in one embodiment, the present invention includes any such muscarinic agent having a contrary effect in diseased tissue such that its effect becomes protective. Accordingly, one aspect of the present invention pertains to providing a method of treatment for muscular dystrophy and related conditions compounds that occur naturally or are designed such that they a.) increase acetylcholine release or b.) inhibit acetylcholinesterase or c.) both a. and b.

In accordance with yet another aspect, the present invention pertains to providing a method of treatment for muscular dystrophy and related condition compounds that occur naturally or are designed such that they mimic acetylcholine and bind to acetylcholine receptors or cause other molecules or compounds to bind to acetylcholine receptors.

Accordingly, the present invention provides as a diagnostic, administration of muscarinic or cholinergic agent by any route (e.g., intrapertonial or topical to the eye) and diagnoses based on contrary physiological response to said agent (e.g., decrease in heart-rate or/and constriction of pupil to atropine in dystrophin-deficient subjects). For example, tropicamide, another muscarinic antagonist, could be applied to the eye; which induces a decrease in pupil size (constriction) in subjects, the opposite of the expected effect, most likely be suggestive of dystrophin-deficiency or other disease resulting in the antagonist actually acting as a cholinomimetic. Likewise, other diseases might affect or be affected by contrary configuration of, or mechanistic pathways involving, the muscarinic receptors, which are sensitive to muscarinic antagonists (e.g., atropine).

In accordance with another embodiment, the present invention is directed to non-invasive methods for diagnosing or aiding in diagnosing a perturbation in the autonomic nervous system in a living human subject. These diagnostic methods take advantage of a new recognition that some aspects of the typical autonomic nervous system disease patient's autonomic nervous system are hypersensitive to neural transmitter mediators (e.g., cholinergic or adrenergic agonists and antagonists). In one method, measurements are made of changes in heart-rate in response to neural transmitter mediators (cholinergic or adrenergic agonists and antagonists) when such mediators are applied at concentrations known to be too low to significantly affect heart-rate in normal individuals. The extent or rate of physiological response of the test individual can also be compared to the extent or rate of the response in an appropriate group of individuals with autonomic nervous system disorder having similar attributes (e.g., age, sex, ethnicity) to the test individual. This group is referred to as a reference group. A similar extent or rate of physiological response in the test individual compared with the reference is indicative of autonomic nervous system disorder in the test individual. The physiological responses and attributes of the test individual and reference can be stored in a database. Optionally, the database can be searched by computer means.

Electronic Apparatus Readable Media and Arrays

Electronic apparatus readable media comprising apparatus to measure a change in heart-rate of the present invention is also provided. As used herein, "electronic apparatus readable media" and "computer readable media," which are used interchangeably herein, refers to any suitable medium for storing, holding or containing data or information that can be read and accessed directly by an electronic apparatus. Such media can include, but are not limited to: magnetic storage media, such as floppy discs, hard disc storage medium, and magnetic tape; optical storage media such as compact disc; electronic storage media such as RAM, ROM, EPROM, EEPROM and the like; general hard disks and hybrids of these categories such as magnetic/optical storage media. The medium is adapted or configured for having recorded thereon a marker of the present invention.

As used herein, the term "electronic apparatus" is intended to include any suitable computing or processing apparatus or other device configured or adapted for storing data or information. Examples of electronic apparatus suitable for use with the present invention include stand-alone computing apparatus; networks, including a local area network (LAN), a wide area network (WAN) Internet, Intranet, and Extranet; electronic appliances such as a personal digital assistants (PDAs), cellular phone, pager and the like; and local and distributed processing systems. As used herein, "recorded" refers to a process for storing or encoding information on the electronic apparatus readable medium.

A variety of software programs and formats can be used to store the heart-rate information of the present invention on the electronic apparatus readable medium. For example, the heart-rate can be represented in a word processing text file, formatted in commercially-available software such as WordPerfect™ and Microsoft Word™, or represented in the form of an ASCII file, stored in a database application, such as DB2, Sybase, Oracle, or the like, as well as in other forms. Any number of data processor structuring formats (e.g., text file or database) may be employed in order to obtain or create a medium having recorded thereon the data generated from the present invention.

The teachings of the present invention therefore provides a medium for holding instructions for performing a method for determining whether a subject has an autonomic nervous system disorder or is at a risk of developing an autonomic nervous system disorder, wherein the method includes the steps of determining the presence or absence of a perturbation of the autonomic nervous system and based on the presence or absence of the perturbation of the autonomic nervous system, determining whether the subject has an autonomic nervous system disorder or is at risk of developing an autonomic nervous system disorder and/or recommending a particular clinical course of therapy or diagnostic evaluation for the autonomic nervous system disorder or pre-disposition to development of the autonomic nervous system disorder condition.

The present invention further provides in an electronic system having a processor and/or in a network, a method for determining whether or not a subject has a perturbation in the autonomic nervous system or a pre-disposition to perturbation in the autonomic nervous system associated with a disorder as described herein wherein the method includes the steps of determining the presence or absence of the change in heart-rate, and based on the presence or absence of the change in heart-rate, determining whether the subject has an autonomic nervous system disorder or a pre-disposition to an autonomic nervous system disorder, and/or recommending a particular treatment for the autonomic nervous system disorder or pre-disposition to the development of autonomic nervous system disorder condition. In one embodiment, the processor implements the functionality of obtaining information from the subject indicative of the presence or absence of neuromuscular disorder. In another embodiment, the processor further implements the functionality of receiving change in heart-rate associated with the cardiac activity of the subject. In yet another embodiment, the processor further implements the functionality of acquiring from a network cardiac activity information associated with the subject. The method may further comprise the step of receiving heart-rate or heart-rate variability associated with the cardiac activity of the subject and/or acquiring from a network heart-rate variability associated with the cardiac activity information associated with the subject.

The teachings of the present invention also provide in a network system, a method for determining whether a subject has perturbation in the autonomic nervous system or a pre-disposition to the development of perturbation in the autonomic nervous system associated with a disorder, said method including the steps of receiving information associated with the heart-rate, receiving phenotypic information associated with the subject, acquiring information from the network corresponding to the heart-rate/heart-rate variability or autonomic nervous system disorder, and based on one or more of the phenotypic information, the heart-rate, and the acquired information, determining whether the subject has an autonomic nervous system disorder or a pre-disposition to an autonomic nervous system disorder. The method may further include the step of recommending a particular treatment for the autonomic nervous system disorder or pre-disposition to the development of autonomic nervous system disorder condition. In one embodiment, the network system includes a server and a workstation operatively connected to the server via the network.

The present invention also provides a method for determining whether a subject has a autonomic nervous system disorder or a pre-disposition to the development of a autonomic nervous system disorder, the method including the steps of receiving information associated with the heart-rate, receiving phenotypic information associated with the subject, acquiring information from the network corresponding to the heart-rate/heart-rate variability and/or autonomic nervous system disorder, and based on one or more of the phenotypic information, the change in heart-rate, and the acquired information, determining whether the subject has autonomic nervous system disorder or a pre-disposition to the development of autonomic nervous system disorder. The method may further include the step of recommending a particular treatment for the autonomic nervous disorder or risk of development of autonomic nervous disorder condition.

In an alternative method, precise measurements are made of pupil constriction in response to stimulation by a cholinergic or a muscarinic agonist or antagonist or a derivative thereof. The method utilizes differences in pupillary dynamic response to stimulation by any of the pharmacologically active agents, described below, between a subject suffering from or at risk of developing an autonomic nervous system disorder and a normal person as a basis and standard for accurately and positively diagnosing an autonomic nervous system disorder (e.g., DMD).

The diagnostic methods described in accordance with the present invention can be used either independently or in combination (for example, the change in heart-rate and constriction of pupil of a subject suffering from or is at risk of suffering from a disorder which correlates with the perturbation of the autonomic nervous system (e.g., a neuromuscular disorder)) so as to provide an accurate, positive and definite diagnosis of the disorder which correlates with perturbation in the autonomic nervous system.

The teachings of the present invention provide an empirical showing that hypersensitivity to neural transmitter mediators is specifically present in those neurons and nerve cell bodies which innervate the muscles that regulate heart beat. Thus, the administration of a neural transmitter mediator or modular (such as cholinergic or adrenergic antagonists or agonists) in a concentration which is generally insufficient to cause a marked or noticeable change in heart-rate in a normal individual will nevertheless cause a change and marked alteration in heart-rate (decrease or increase) in the person afflicted with a neuromuscular disorder (e.g., a neuromuscular disease)

An apparatus suitable for use in accordance with the teachings of the present invention can be found in U.S. patent application Ser. No. 09/523,770, filed Mar. 11, 2000, which is incorporated herein by reference.

Pharmaceutical Compositions

The scientific basis for the present diagnostic methods is the recognition that persons afflicted with autonomic nervous system disorder are uniquely hypersensitive to the pharmacological effects of neural transmitter mediators, such as atropine, which are administered intraperitoneally. Other modes of administration, such as, intravenously, buccal, intracoronary, intramuscularly, topically, intranasally, rectally, sublingually, orally, subcutaneously, by patch, or inhalation are also encompassed by the present invention. An alternatively preferred mode of administration is topically administering the neural transmitter mediators topically in the eye (ophthalmologically).

The existence of such hypersensitivity, however, is not only an intrinsic part of the disease process but also can be intentionally manipulated pharmacologically in the person afflicted with a neuromuscular disease (e.g., DMD). Thus, the underlying principles for the present invention are first, that this unique hypersensitive state exists and manifests itself in the autonomic nervous system of a patient suffering from a neuromuscular disorder; and second, that this hypersensitive state will manifest itself as an abnormal response to pharmacologically active antagonists and agonists in a distinctive manner which can be utilized for diagnostic purposes.

An intrinsic part of the DMD process is hypersensitivity to neural transmitters affecting the heart-rate; and the concomitant demonstration that pharmacologically active mediators can be employed to manipulate this disease condition and to yield a hypersensitive alteration in heart-rate response.

There are many physiological responses on which the diagnostic test for DMD of the present embodiment can be based. Suitable physiological responses include those under the neuromuscular control of cholinergic antagonists, adrenergic agonists or adrenergic antagonists. One suitable physiological response is a change in heart-rate. Other suitable physiological responses include change in pupil diameter, sweat production, saliva production, and blood pressure. Physiological responses are generally chosen to maximize the ease of assessing the degree of the response.

Agents suitable for use in the method of the present embodiment for diagnosing an individual suffering from a disorder which correlates with perturbation in the autonomic nervous system (e.g., a neuromuscular disorder such as DMD) include cholinergic agonists or antagonists, adrenergic agonists or antagonists, acetylcholinesterase inhibitors, agonists and antagonists of intracellular signaling systems, agonists and antagonists of neuromodulatory systems, agonists and antagonists of calcium metabolism and calcium channels, agonist and antagonists of sodium and potassium channels involved in nerve and muscle function.

Suitable cholinergic antagonists which can be tested for use as a diagnostic for DMD include atropine, latrotoxin, tropicamide, pirenzepine, popanthelein, scopolamine, quinuclidinyl benzilate, bungarotoxin, cobratoxin, pancuronium, curare and the derivatives thereof. Suitable adrenergic agonists which can be tested for use as a diagnostic for a disorder resulting from perturbation of autonomic nervous system include epinephrine, clonidine and the derivative thereofs. Suitable adrenergic antagonists which can be tested for use as a diagnostic for a disorder resulting from perturbation of autonomic nervous system include propranolol, phentolamine and their derivative.

Numerous other compounds have been identified that act as either agonists (e.g., Muscarine, Nicotine) or antagonists (e.g., Botulinus Toxin, α-Bungarotoxin, δ-Tubocurarine) of cholinergic neurons. The principal action of cholinergic agonists is the excitation or inhibition of autonomic effector cells that are innervated by postganglionic parasympathetic neurons and as such are referred to as parasympathomimetic agents. The cholinergic agonists also include choline esters (such as ACh itself) as well as protein- or alkaloid-based compounds. Several naturally occurring compounds have been shown to affect cholinergic neurons, either positively or negatively.

The responses of cholinergic neurons can also be enhanced by administration of cholinesterase (ChE) inhibitors. ChE inhibitors have been used as components of nerve gases but also have significant medical application in the treatment of disorders such as glaucoma and myasthenia gravis as well as in terminating the effects of neuromuscular blocking agents such as atropine.

Suitable acetylcholinesterase inhibitors include tacrine, physostigmine, DFP (diisofluorophosphate), and related compounds.

Suitable agonists of intramolecular signaling systems include forskolin. Suitable antagonists of intramolecular signaling systems include lithium and pertussis toxin. Also included in intramolecular signaling systems are agonists and antagonist of kinases and phosphatases, okadaic acid, phorbol esters and the derivatives thereof.

Suitable agonists and antagonists of neuromodulatory systems include those agonists and antagonists which modulate systems involving amines (such as serotonin and dopamine), peptide hormones, adenosine, gamma-amino butyric acid (GABA), glutamate, nitric oxide, carbon monoxide and the like. Agents which act as agonists for the receptors of these systems include N-methyl d-aspartate (NMDA), kainate, benzodiazepines, barbiturates, thioxanthene and the like. Agents which act as antagonists for the receptors of these systems include clozapine, phenothiazine reserpine, and the like. Also included are antagonists and agonists which modulate the uptake and processing of neurotransmitters. Examples of such antagonists include cocaine, Prozac, imipramine, fluoxetine, clorgyline, reserpine, amphetamine, pargyline, Rolpram, and the derivatives thereof.

Calcium metabolism and calcium channels, as used herein, refers to voltage-sensitive calcium channels, the N-methyl d-aspartate receptor and inositol triphosphate dependent release of calcium from intracellular stores. Suitable agonists include N-methyl d-aspartate, glutamate and lithium. Suitable antagonists include APV (2-amino-5-phosphonovalerate), conotoxin, various spider toxins, nitrendopine, dihydropyridine, digitalis, and the derivatives thereof.

The above agents can be incorporated into pharmaceutical compositions suitable for administration to a subject, e.g., a human. Such compositions typically comprise a pharmaceutically acceptable carrier. As used herein the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, such media can be used in the compositions of the invention. Supplementary active compounds can also be incorporated into the compositions.

A pharmaceutical composition of the invention is formulated to be compatible with its intended route of administration.

The manner in which the compounds are administered can vary. The compounds can be administered by inhalation (e.g., in the form of an aerosol either nasally or using delivery articles of the type set forth in U.S. Pat. No. 4,922,901 to Brooks et al.); topically (e.g., in lotion form); orally (e.g., in liquid form within a solvent such as an aqueous or non-aqueous liquid, or within a solid carrier); ophthalmologically (e.g., as an ointment or an eyedrop in a liquid form as described above); intravenously (e.g., within a dextrose or saline solution); as an infusion or injection (e.g., as a suspension or as an emulsion in a pharmaceutically acceptable liquid or mixture of liquids); or transdermally (e.g., using a transdermal patch). Although it is possible to administer the compounds in the form of a bulk active chemical, it is preferred to present each compound in the form of a pharmaceutical composition or formulation for efficient and effective administration. Exemplary methods for administering such compounds will be apparent to the skilled artisan. For example, the compounds can be administered in the form of a tablet, a hard gelatin capsule or as a time release capsule. As another example, the compounds can be delivered transdermally using the types of patch technologies available from Ciba-Geigy Corporation and Alza Corporation. The administration of the pharmaceutical compositions of the present invention can be intermittent, or at a gradual, continuous, constant or controlled rate to a warm-blooded animal, such as a human being. In addition, the time of day and the number of times per day that the pharmaceutical formulation is administered can vary. Administration preferably is such that the active ingredients of the pharmaceutical formulation interact with receptor sites within the body of the subject that effect the functioning of the autonomic nervous system.

The dose of the compound is that amount effective to prevent occurrence of the symptoms of the disorder or to treat some symptoms of the disorder from which the patient suffers. By "effective amount", "therapeutic amount" or "effective dose" it is meant the amount sufficient to elicit the desired pharmacological or therapeutic effects, thus resulting in effective diagnosis or treatment of the disorder. Thus, an effective amount of compound is an amount sufficient to pass across the blood-brain barrier of the subject, to bind to relevant receptor sites in the brain of the subject, and to elicit neuropharmacological effects (e.g., elicit neurotransmitter secretion, thus resulting in effective diagnosis or treatment of the disorder). Diagnosis of the disorder is manifested by delaying the onset of the symptoms of the disorder. Treatment of the disorder is manifested by a decrease in the symptoms associated with the disorder or an amelioration of the reoccurrence of the symptoms of the disorder.

Compounds of the present invention, when employed in effective amounts in accordance with the method of the present invention, are effective towards providing some degree of diagnosis of the progression of autonomic nervous system disorders, amelioration of the symptoms of autonomic nervous system disorders, and amelioration to some degree of the reoccurrence of autonomic nervous system disorders. However, such effective amounts of those compounds are not sufficient to elicit any appreciable side effects, as demonstrated by increased effects relating to the cardiovascular system, and effects to skeletal muscle. As such, administration of compounds of the present invention provides a therapeutic window in which treatment of certain autonomic nervous system disorders is provided, and side effects are avoided. That is, an effective dose of a compound of the present invention is sufficient to provide the desired effects upon the autonomic nervous system, but is insufficient (i.e., is not at a high enough level) to provide undesirable side effects. Preferably, effective administration of a compound of the present invention results in treatment of autonomic nervous system disorders with minimal side effects.

EXAMPLES

Methods

Mice

Male control C57BL/10ScSn (C57, n=15) and male mutant (mdx, n=15) mice (10–12 weeks old) were obtained from The Jackson Laboratory, Bar Harbor, Me. The animals were housed in standard conditions within the Animal Resource Facility at the Beth Israel Deaconess Medical Center. Handling and care of mice were consistent with federal and institutional guidelines.

ECG Recording

ECGs were recorded in conscious mice as follows. Briefly, mice were gently removed from their cages and positioned on the ECG recording platform (AnonyMOUSE, Mouse Specifics, Inc., Boston, Mass.). An array of gel-coated ECG electrodes were embedded in the floor of the platform and spaced to provide contact between the electrodes and animals' paws. The electrodes were connected to an amplifier by three shielded conductive leads. As even modest handling of mice induces significant alterations in heart-rate, each mouse was permitted to acclimatize for 10 min prior to collection of baseline data. The signals were digitized with 16-bit precision at a sampling rate of 2000 samples/second. When mice were sitting or otherwise positioned such that the paws were not in contact with three electrodes, the output from the amplifier was discarded. Only data from continuous recordings of 15–25 ECG signals were used in the analyses.

ECG Analyses

Analyses of the ECGs were performed as described as follows. Each signal was analyzed using e-MOUSE, internet-based physiologic waveform analyses software. The program incorporates Fourier analyses and linear time-invariant digital filtering of frequencies below 2 Hz and above 100 Hz to minimize signal environmental disturbances. The software uses a peak detection algorithm to find the peak of the R-waves and to calculate heart-rate (HR). The inverted and/or biphasic portions of the T wave was included in calculations of the QT interval. The QT intervals were rate corrected (QTc) by an algorithm developed for use in mice. The software plots its interpretation of P, Q, R, S, and T for each beat so that spurious data resulting from unfiltered noise or motion artifacts may be rejected. The mean of the ECG time intervals for each set of waveforms is then calculated.

Time-Domain Measures of Heart-Rate Variability

Heart-rate variability (HRV) was calculated as the standard deviation of all R—R intervals for each set of ECG signals. The coefficient of variance (CV,%) was calculated as the ratio of mean HRV to mean heart-rate.

Autonomic Blockade

Parasympathetic and sympathetic nervous system control of heart-rate regulation were investigated by pharmacological blockade. Mice received intraperitoneal administration of atropine (0.5 mg/kg) for parasympathetic blockade (n=15 mdx, n=15 C57), propranolol (1 mg/kg) for sympathetic blockade (n=10 mdx, n=7 C57), and atropine (0.5 mg/kg) plus propranolol (1 mg/kg) for combined β-adrenergic and muscarinic cholinergic blockade (n=10 mdx, n=7 C57). Baseline ECGs were recorded within 5 min prior to each administration and after a 5–10 min equilibrium phase after drug administration to allow for HR stabilization. The pharmacological interventions were performed on different days to prevent interference between drugs. The dosages of atropine and propranolol were those used by others investigating autonomic blockade in conscious mice.

Baroreflex HR Modulation

Mice were administered intraperitoneal phenylephrine (3 mg/kg) after β-adrenergic blockade with propranolol (1 mg/kg) to test for a baroreflex-mediated cardio-inhibitory response (n=10 mdx, n=7 C57).16,21 After baseline recordings, ECGs were recorded after a 5–10 min equilibrium phase following propranolol administration to allow for HR stabilization, and then within 2 min following phenylephrine administration. Changes in ECG indices following phenylephrine were determined relative to those recorded following propranolol administration.

Role of Neuronal Nitric Oxide

To investigate whether our observations were linked to deficiency in neuronal nitric oxide, we performed similar protocols as described above in mice deficient in nNOS (nNOS -/-, n=7) and B6129SF2/J control mice (B6129, n=6). These mice were obtained from The Jackson Laboratories (Bar Harbor, Me.) and were housed and cared for as described above.

Statistics

Data are presented as the means±SE. Comparisons between mdx and C57 mice and between nNOS -/- and B6129 mice were performed using Student's t-test for unpaired observations. Effects of autonomic blockade or baroreflex sensitivity testing within groups were performed using Student's t-test for paired observations, and between group comparisons using Student's t-test for unpaired observations. Differences were considered significant with $P<0.05$.

Example 1 mdx Mice Lacking Dystrophin Exhibit a Different Baseline HR Dynamics as Compared to Control Mice The change in heart-rate, heart-rate variability, and the altered autonomic nervous system control of heart-rate modulation were studied in mice deficient in dystrophin (mdx) and in wild-type control mice (C57B). Table 1 summarizes the ECG data in mdx and C57 control mice. At baseline, HR was significantly higher in mdx mice compared to C57 mice. The mdx mice had significantly shorter QRS duration, shorter QT interval, and shorter QTc interval compared to C57 mice. At baseline, PR interval was significantly shorter in mdx mice, and HRV and CV were significantly lower in mdx than C57 mice. FIG. 1 illustrates representative ECG recordings from a C57 control mouse (top panel) and an mdx mouse (bottom panel). Since the mice are conscious and ambulatory, baseline artifact and noise are apparent in the unfiltered signals. Nevertheless, the P wave and T waves are discernible and interpretable by the software algorithmic processing of the signal digitized at 2000 samples per second. These results demonstrate that mice deficient in dystrophin have increased heart-rates, decreased heart-rate variability, and altered autonomic nervous system control of heart-rate modulation in comparison to wild-type control mice.

TABLE 1

Baseline electrocardiographic parameters and time-domain measures of heart rate variability in C57 and mdx conscious mice.

|  | C57 (n = 15) | mdx (n = 15) |
|---|---|---|
| Heart Rate (bpm) | 706 ± 13 | 809 ± 5* |
| HRV (ms) | 2.7 ± 0.9 | 0.5 ± 0.1* |
| CV (%) | 2.9 ± 0.9 | 0.7 ± 0.1* |
| PR (ms) | 29.4 ± 0.5 | 27.2 ± 0.4* |
| QRS (ms) | 8.3 ± 0.2 | 7.5 ± 0.1* |
| QT (ms) | 57.2 ± 2.0 | 47.8 ± 0.5* |
| $QT_c$ (ms) | 61.6 ± 1.5 | 55.5 ± 0.5* |

Values are mean ± SE.
HRV, heart rate variability.
CV, coefficient of variance.
*, P < 0.05.

Example 2

Autonomic Nervous System Blockade

Figure 2A:
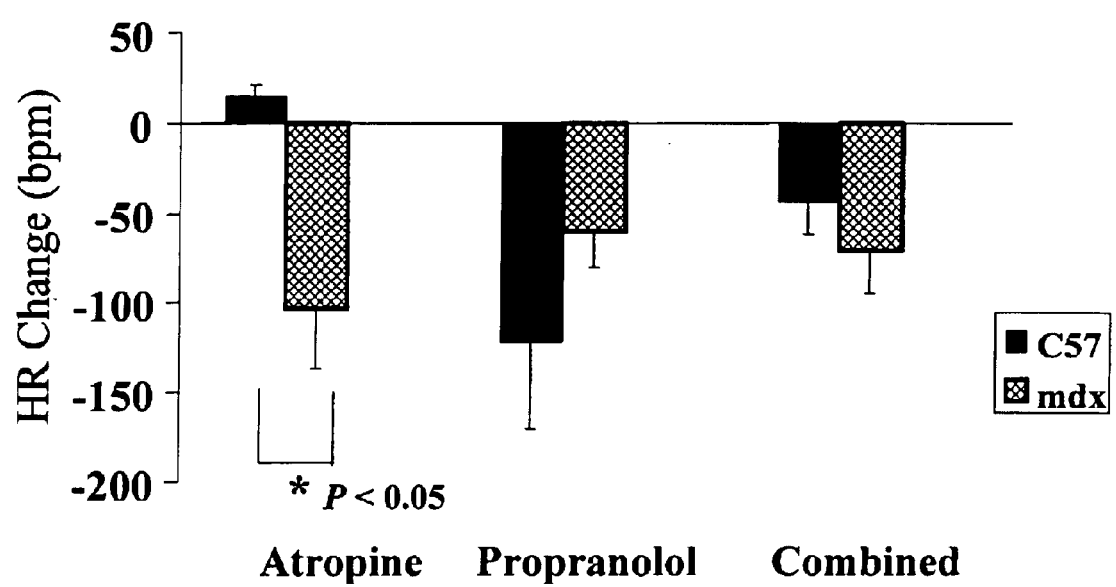
FIG. 2a illustrates in vivo response of HR to atropine, propranolol, and the combination of both drugs. Agents were administered on three separate days. After atropine administration, HR decreased 90±14 bpm in mdx mice, whereas HR increased 21±12 bpm in C57 mice (P<0.05).
Figure 2B:
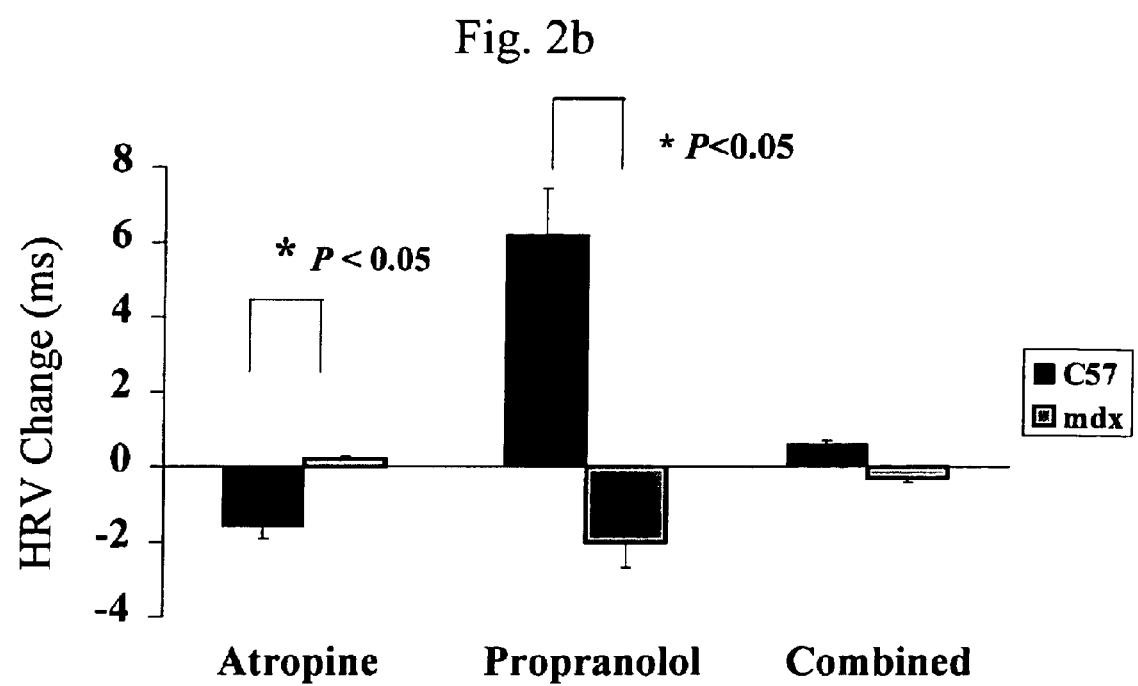
FIG. 2b illustrates in vivo response of HRV to atropine, propranolol, and the combination of both drugs. Agents were administered on three separate days. After atropine administration, HRV significantly decreased in C57 mice, from 2.7±0.9 ms to 0.5±0.9 ms, but did not change in mdx mice.

To study the effect of autonomic blockers on dystrophin deficient mice, parasympathetic and sympathetic nervous system control of heart-rate regulation were investigated by pharmacological blockade. Mice received intraperitoneal administration of atropine (0.5 mg/kg) for parasympathetic blockade (n=15 mdx, n=15 C57), propranolol (1 mg/kg) for sympathetic blockade (n=10 mdx, n=7 C57), and atropine (0.5 mg/kg) plus propranolol (1 mg/kg) for combined β-adrenergic and muscarinic cholinergic blockade (n=10 mdx, n=7 C57). Baseline ECGs were recorded within 5 min prior to each administration and after a 5–10 min equilibrium phase after drug administration to allow for HR stabilization. The pharmacological interventions were performed on different days to prevent interference between drugs. Compared to the effects in C57 mice, atropine administration in mdx mice led to significantly greater changes in HR (−90±14 bpm vs. +21±12 bpm, P<0.05) and significantly smaller changes in HRV (+0.1±10.1 ms vs. −1.6±0.7 ms, P<0.05). Heart-rate decreased in all 15 mdx mice after administration of atropine, whereas heart-rate increased in all but 2 of the C57 mice after administration of atropine. Propranolol administration exerted a more modest reduction in heart-rate in mdx mice (−60±27 bpm, n=10) than C57 mice (−122±53 bpm, n=7) (P=NS). The change in HRV following propranolol was more significant in C57 than mdx mice (P<0.05). Parasympathetic, sympathetic, and combined blockade on HR and HRV are shown in FIGS. 2a and 2b. Autonomic blockade resulted in a slightly larger decrease in HR in mdx than C57 mice such that there was no longer any difference in mean HR between the two groups after atropine and propranolol administration. The effects of combined sympathetic and parasympathetic autonomic blockade on HRV were similar in mdx and C57 mice.

Example 3

Baroreflex Pressor Response

The HR response to phenylephrine in C57 (n=7) and mdx mice (n=10) were examined. Mice were administered intraperitoneal phenylephrine (3 mg/kg) after β-adrenergic blockade with propranolol (1 mg/kg) to test for a baroreflex-mediated cardio-inhibitory response (n=10 mdx, n=7 C57). After baseline recordings, ECGs were recorded after a 5–10 min equilibrium phase following propranolol administration to allow for HR stabilization, and then within 2 min following phenylephrine administration. Changes in ECG indices following phenylephrine were determined relative to those recorded following propranolol administration.

Figure 3A:
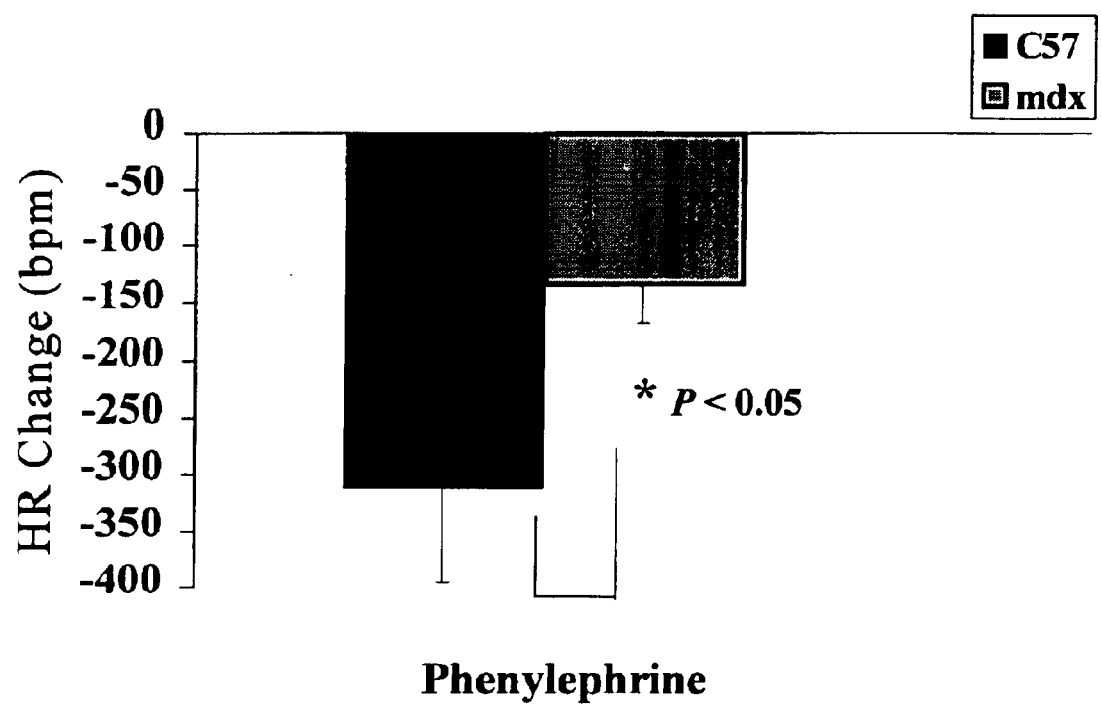
FIG. 3a illustrates in vivo baroreflex response to phenylephrine in mdx and C57 mice. The reduction in HR after phenylephrine administration was significantly attenuated in mdx mice (−132±27 bpm) compared to C57 mice (−312±27 bpm) (P<0.05).

The pressor challenge was performed after β-adrenergic blockade so that an observed change in HR or HRV could be attributed to activation of the inhibitory limb of the baroreflex and not the result of sympathetic withdrawal. As shown in FIGS. 3a and 3b, mdx mice administered phenylephrine demonstrated significantly smaller reductions in HR and similar changes in HRV compared to C57 mice. After phenylephrine administration, HRV remained significantly smaller in mdx than C57 mice (8.5±2.5 ms vs. 28.6±4.1 ms, P<0.05) and CV remained significantly smaller in mdx than C57 mice (6.0±1.7% vs. 15.8±2.4%, P<0.05).

Example 4

Effects of nNOS Deficiency

Figure 4A:
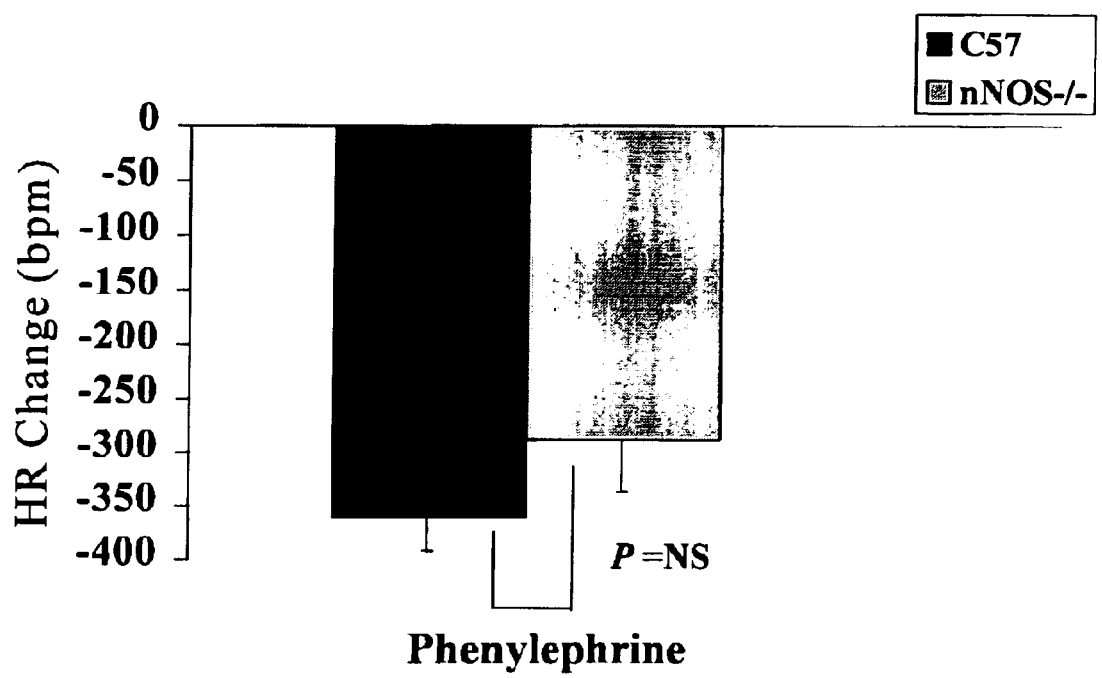
FIG. 4a illustrates in vivo baroreflex response to phenylephrine in nNOS -/- and B6129 mice. Phenylephrine administration resulted in an equivalent reduction in HR in nNOS -/- (−288±39 bpm) and B6129 mice (−360±6 bpm) (P=NS).
Figure 5:
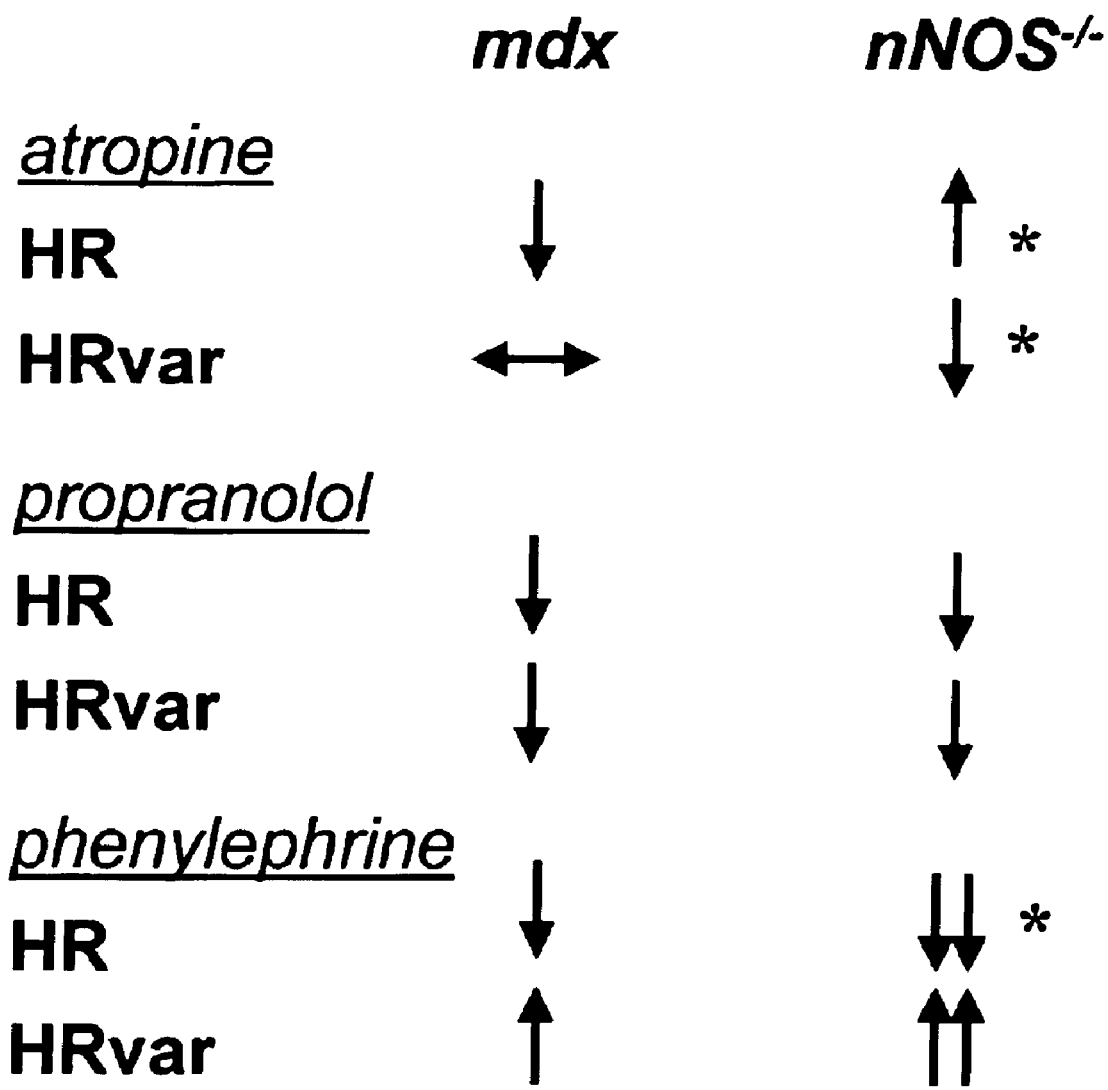
FIG. 5 schematically describes directional changes in HR and HRV in dystrophin-deficient and nNOS-deficient mice in response to autonomic blockade and pressor challenge. mdx and nNOS -/- exhibited sharply different responses, suggesting that the response in mdx mice may be independent of nNOS downregulation. *P<0.05 indicates significant differences between nNOS -/- and mdx mice in response to drug administration.

To investigate if deficiency in neuronal nitric oxide had a role in above observations, similar experiments, as described above, were performed in mice deficient in nNOS (nNOS -/-, n=7) and B6129SF2/J control mice (B6129, n=6). These mice were obtained from The Jackson Laboratories (Bar Harbor, Me.) and were housed and cared for as described above. Seven male nNOS -/- mice and six male B6129 control mice were subjected to the same protocols described above. As reported in Table 2, HR was significantly lower in nNOS -/- mice compared to B6129 control mice. At baseline, heart-rate variability tended to be greater in nNOS -/- in comparison to B6129 mice. After atropine was administered to nNOS -/- mice, HR increased (from 686±22 bpm to 721±12 bpm, P=0.07), HRV significantly decreased (from 2.6±0.1 ms to 0.7±0.1 ms, P<0.05), and CV significantly decreased (from 2.7±0.8% to 0.8±0.1%, P<0.05). In nNOS -/- mice, β-adrenergic blockade significantly reduced HR by 17±6 bpm (P<0.05) and combined autonomic blockade reduced HR by 112±3 bpm (P<0.05). As shown in FIGS. 4a and 4b, phenylephrine administration resulted in equivalent reductions in HR (−288±39 bpm vs. −360±6 bpm, P=NS) and equivalent increases in HRV (+13.3±3.7 ms vs. +11.8±3.7 ms, P=NS) in nNOS -/- and B6129 mice. After phenylephrine administration, HRV was equivalent in nNOS -/- and B6129 mice. FIG. 5 indicates the directional differences between mdx and nNOS -/- mice in response to autonomic blockade. Atropine significantly decreased HR in mdx mice, whereas it significantly increased HR in nNOS -/- mice. Atropine significantly decreased HRV in nNOS -/- mice, whereas it had no effect on HRV in mdx mice. Propranolol had comparable depressant effects on HR and HRV in mdx and nNOS -/- mice. The baroreflex response after administration of phenylephrine was significantly blunted in mdx mice compared to the response in nNOS -/- mice.

TABLE 2

Baseline electrocardiographic parameters and time-domain measures of heart rate variability in B6129SF2/J and nNOS$^{-/-}$ conscious mice.

|  | B6129 (n = 6) | nNOS$^{-/-}$ (n = 7) |
|---|---|---|
| Heart Rate (bpm) | 765 ± 10 | 686 ± 22* |
| HRV (ms) | 0.8 ± 0.2 | 2.6 ± 0.8 |
| CV (%) | 1.1 ± 0.2 | 2.7 ± 0.8 |
| PR (ms) | 29.4 ± 0.8 | 27.7 ± 0.4 |
| QRS (ms) | 7.8 ± 0.1 | 8.6 ± 0.2* |

TABLE 2-continued

Baseline electrocardiographic parameters and time-domain measures of heart rate variability in B6129SF2/J and nNOS$^{-/-}$ conscious mice.

|  | B6129 (n = 6) | nNOS$^{-/-}$ (n = 7) |
|---|---|---|
| QT (ms) | 49.9 ± 0.5 | 60.8 ± 2.9* |
| QT$_c$ (ms) | 56.3 ± 0.4 | 64.8 ± 2.0* |

Values are mean ± SE.
HRV, heart rate variability.
CV, coefficient of variance.
*, P < 0.05.

Equivalents

Although the invention has been described with reference to its preferred embodiments, other embodiments can achieve the same results. Those skilled in the art will recognize or be able to ascertain using no more than routine experimentation, numerous equivalents to the specific embodiments described herein. Such equivalents are considered to be within the scope of the present invention and are encompassed by the following claims.

References

1. Ashford A, Penn G B, Ross J W, Cholinergic activity of atropine. Nature 1962;193:1082–1083.
2. Bia B L, Cassidy P J, Young M E, Rafael J A, Leighton B, Davies K E, Radda G K, Clarke K. Decreased myocardial nNOS, increased iNOS and abnormal ECGs in mouse models of Duchenne muscular dystrophy. J Mol Cell Cardiol 1999;31:1857–1862.
3. Blizard D A, Welty R. Cardiac activity in the mouse: strain differences. J Compar Physiol Psychol 1971;77:337–344.
4. Boland B J, Silbert P L, Groover R V, Wollan P C, Silverstein M D. Skeletal, cardiac, and smooth muscle failure in Duchenne muscular dystrophy. Pediatr Neurol 1996;14:7–12.
5. Brandle M, Wang W, Zucker I H. Hemodynamic correlates of baroreflex impairment of heart-rate in experimental canine heart failure. Basic Res Cardiol 1996;91:147–154.
6. Brenman J E, Chao D S, Xia H, Aldape K, Bredt D S. Nitric oxide synthase complexed with dystrophin and absent from skeletal muscle sarcolemma in Duchenne muscular dystrophy. Cell 1995;82:743–752.
7. Bulfield G, Siller W G, Wight P A L, Moore K J. X chromosome-linked muscular dystrophy (mdx) in the mouse. Proc Nat Acad Sci USA 1984;81:1189–1192.
8. Chang W, Iannaccone T, Lau K, Masters B S S, McCabe T J, McMillan K, Padre R C, Spencer M J, Tidball J G, Stull J T. Neuronal nitric oxide synthase and dystrophin-deficient muscular dystrophy. Proc Natl Acad Sci USA 1996;93:9142–9147.
9. Chao D S, Silvagno F, Bredt D S. Muscular dystrophy in mdx mice despite lack of neuronal nitric oxide synthase. J Neurochem 1998;71:784–789.
10. Chen Y W, Zhao P, Borup R, Hoffman E P. Expression profiling in the muscular dystrophies: identification of novel aspects of molecular pathophysiology. J Cell Biol 2000;151:1321–1336.
11. Chu V, Otero J M, Lopez O, Morgan J P, Amende I, Hampton T G. Method for non-invasively recording electrocardiograms in conscious mice. BioMedCentral Physiology 2001;1:6.
12. Cox G F, Kunkel L M. Dystrophies and heart disease. Curr Opin Cardiol 1997;12:329–343.
13. Danko I, Chapman V, Wolff J A. The frequency of revertants in mdx mouse genetic models for Duchenne muscular dystrophy. Pediatr Res 1992;32:128–131.
14. Das G, Talmers F N, Weissler A M. New observations on the effects of atropine on the sinoatrial and atrioventricular nodes in man. Am J Cardiol 1975;36:281–285.
15. Desai K H, Sato R, Schauble E, Barish G S, Kobilka B K, Berstein D. Cardiovascular indexes in the mouse at rest and with exercise: new tools to study models of cardiac disease. Am J Physiol Heart Circ Physiol 1997;272:H1053–H1061.
16. Gehrmann J, Hammer P E, Maguire C T, Wakimoto H, Triedman J K, Berul C I. Phenotypic screening for the heart-rate variability in the mouse. Am J Physiol Heart Circ Physiol 2000;279:H733–H740.
17. Gieseler K, Mariol M C, Bessou C, Migaud M, Franks C J, Holden-Dye L, Segalat L. Molecular, genetic and physiological characterization of dystrobrevin-like (dyb-1) mutants of Caenorhabditis elegans. J Mol Biol 2001;307:107–117.
18. Gilroy J, Cahalan J, Berman R, Newman M. Cardiac and pulmonary complications in Duchenne's progressive muscular dystrophy. Circulation1963;1:484–493.
19. Grady M R, Teng H, Nichol M C, Cunningham J C, Wilkinson R S, Sanes J R. Skeletal and cardiac myopathies in mice lacking utrophin and dystrophin: A model for Duchenne muscular dystrophy. Cell 1997;90:729–738.
20. Johansson C, Vennstrom B, Thoren P. Evidence that decreased heart-rate in thyroid hormone receptor-α-deficient mice is an intrinsic effect. Am J Physiol Reg Integ Comp Physiol 1998;275:R640–R646.
21. Jumrussirikul P, Dinerman J, Dawson T M, Dawson V L, Ekelund U, Georgakopoulos D, Schramm L P, Calkins H, Snyder S H, Hare J M, Berger M D. Interaction between neuronal nitric oxide synthase and inhibitory G protein activity in heart-rate regulation in conscious mice. J Clin Inv 1998;102:1279–1285.
22. Kato G. NMR studies on drug receptor interactions. Int J Clin Pharmacol 1971;5:12–19.
23. Kramer K, van Acker V, Sabe, Voss H-P, Grimbergen J A, van der Vijgh W J F, Bast A. Use of telemetry to record electrocardiogram and heart-rate in freely moving mice. J Pharmacol Toxicol Methods 1993;30:209–215.
24. Lönnerholm G, Widerlöv E. Effect of intravenous atropine and methylatropine on heart-rate and secretion of saliva in man. Eur J Clin Pharmacol 1975;8:233–240.
25. Lu S, Hoey A. Changes in function of cardiac receptors mediating the effects of the autonomic nervous system in muscular dystrophy (mdx) mouse. J Mol Cell Cardiol 2000;32:143–152.
26. Mancinelli E, Sardini A, D'Aumiller A, Meola G, Martucci G, Cossu G, Wanke E. Properties of acetylcholine-receptor activation in human Duchenne muscular dystrophy myotubes. Proc R Soc Lond B Biol Sci 1989;237:247–257.
27. Marcello N, Baratti M, Ortaggio F, Vescovini E, Zanoni P, Tugnoli V, De Grandis D. Autonomic function and the sinus tachycardia of Duchennne Muscular Dystrophy. Electromyogr Clin Neurophysiol 1995;35:387–395.
28. Marselos M, Eriksson K, Hanninen O. Effects of β-adrenoceptor blocking drugs, physostigmine, and atropine on the toxicity of doxepin in mice. Med Biol 1975;53:231–237.
29. Maruyama T, Fujino T, Fukuoka Y, Tsukamoto K, Mawatarti S. Notched T wave as evidence of autonomic nervous lability in Duchenne progressive muscular dystrophy. Jpn Heart J 1995;36:741–750.
30. Megeney L A, Kablar B, Perry R L S, Ying C, May L, Rudnicki M A. Severe cardiomyopathy in mice lacking dystrophin and MyoD. Proc Natl Acad Sci USA 1999;96:220–225.
31. Miller G, D'Orsogna L, O'Shea J P. Cardiomyopathy of Duchenne muscular dystrophy. Brain Dev 1989;11:247–250.

32. Mitchell G F, Jeron A, Gideon K. Measurement of heart-rate and Q-T interval in the conscious mouse. Am J Physiol Heart Circ Physiol 1998; 274:H747–H751.
33. Nigro G, Comi L I, Politano L, Bain R J I. The incidence and evolution of cardiomyopathy in Duchenne muscular dystrophy. Int J Cardiol 1990;26:271–277.
34. Perloff J K. Cardiac rhythm and conduction in Duchenne's muscular dystrophy: A prospective study in 20 patients. J Am Coll Cardiol 1984;3:1263–1268.
35. Perloff J K. Neurological disorders and heart disease. In: Braunwald E, editor. Heart disease. Philadelphia: W. B. Saunders Co. 1998;1782–1783.
36. Radda G K. Of mice and men: from early NMR studies of the heart to physiological genomics. Biochem Biophys Res Commun 1999;266:723–728.
37. Sanyal S K, Johnson W W, Thapar M K, Pitner S E. An ultrastructural basis for electrocardiographic alterations associated with Duchenne's progressive muscular dystrophy. Am J Cardiol 1978;6:1122–1129.
38. Sapp J L, Bobet J, Howlett S E. Contractile properties of myocardium are altered in dystrophin-deficient mdx mice. J Neurol Sci 1996;142:17–24.
39. Schwarz P J, Stone H L. The role of the autonomic nervous system in sudden coronary death. Ann NY Acad Sci 1982;382:162–180.
40. Sekiya A. Action of atropine on rabbit blood cholinesterase. Jpn J Pharmacol 1954;4:22–23.
41. Slucka C. The electrocardiogram in Duchenne progressive muscular dystrophy. Circulation 1968;38:933–940.
42. Stewart J M. Autonomic nervous system dysfunction in adolescents with postural orthostatic tachycardia syndrome and chronic fatigue syndrome is characterized by attenuated vagal baroreflex and potential sympathetic vasomotion. Pediatr Res 2000;48:218–226.
43. Swynghedauw B, Jasson S, Chevalier B, Clairambault J, Hardouin S, Heymes C, Mangin L, Mansier P, Médigue C, Moalic J, Thibault N, Carré F. Heart-rate and heart-rate variability a pharmacological target. Cardiovasc Drugs Ther 1996;10:677–685.
44. Torres L F B, Duchen L W. Morphological studies of nerves, muscles and end-plates. Brain 1987;110:269–299.
45. Tsuji H, Venditti F J, Manders E S, Evans J C, Larson M G, Feldman C L, Levy D. Determinants of heart-rate variability. J Am Coll Cardiol 1996;28:1539–1546.
46. Tuli J S, Smith A, Morton D B. Stress measurements in mice after transportation. Lab Anim 1995;29:132–138.
47. Uechi M, Asai K, Osaka M, Smith A, Sao N, Wagner T E, Ishikawa Y, Hayakawa H, Vatner D E, Shannon R P, Homcy C J, Vatner S F. Depressed Heart-rate variability and arterial baroreflex in conscious transgenic mice with over-expression of cardiac Ga. Circ Res 1998;82:416–423.
48. Wahi P L. Cardiac changes in myopathy. Am Heart J 1963;66:749–751.
49. Wellstein A, Pitschner H F. Complex dose-response curves of atropine in man explained by different functions of M1- and M2-cholinoceptors. Naunyn-Schmiedebergs Arch Pharmacol 1988;338:19–27.
50. Wetzel G T, Brown J H. Presynaptic modulation of acetylcholine release from cardiac parasympathetic neurons. Am J Physiol 1985;248:H33–H95.
51. Wickman K, Nemec J, Gendler S, Clapham D. Abnormal heart-rate regulation in GIRK4 knockout mice. Neuron 1998;20:103–114.
52. Yotsukura M, Fujii K, Katayama A, Tomono Y, Ando H, Sakata K, Ishihara T, Ishikawa K. Nine-year follow-up study of heart-rate variability in patients with Duchenne-type progressive muscular dystrophy. Am Heart J 1998;136:289–296.
53. Yotsukura M, Sasaki K, Kachi E, Sasaki A, Ishihara T, Ishikawa K. Circadian rhythm and variability of heart-rate in Duchenne-type progressive muscular dystrophy. Am J Cardiol 1995;76:947–951.

What is claimed is:

1. A method of diagnosing or aiding in diagnosing Duchenne muscular dystrophy in a subject, the method comprising the steps of:
   a) administering to said subject, an effective amount of a cholinergic agent or a derivative thereof; and,
   b) determining whether the cholinergic agent or a derivative thereof, induces a decrease in the heart-rate of the subject in response to the cholinergic agent or a derivative thereof:
   wherein a decrease in said heart rate is indicative that said subject has Duchenne muscular dystrophy.

2. The method of claim 1, wherein the decrease in the heart rate is determined using a detector supplying data associated with electrocardiogram signals and providing an electrocardiogram using an apparatus for interpreting the data associated with electrocardiogram signals of the subject.

3. The method of claim 1, wherein the decrease in heart rate activity is detected by a computing apparatus.

4. The method of claim 3, wherein the computing apparatus further comprises a digital processor, a working memory, and a database, which records changes in heart rate in the subject.

5. The method of claim 1, wherein the perturbation is caused by an alteration in property and function of an acetylcholine receptor.

6. The method of claim 1, wherein the perturbation is caused by an alteration in property and function of a cholinergic receptor.

7. The method of claim 6, wherein the cholinergic receptor is a muscarinic receptor.

8. The method of claim 1, wherein the perturbation is caused by a perturbation in acetylcholine concentration.

9. The method of claim 1, wherein the perturbation is caused by perturbation in acetylcholinesterase concentration.

10. The method of claim 1, wherein the perturbation is caused by a deficiency in dystrophin or a dystrophin-associated protein.

11. The method according to claim 1, wherein the cholinergic agent or a derivative thereof, is a muscarinic agent.

12. The method claim 11, wherein the muscarinic agent is a muscarinic antagonist or a derivative thereof.

13. The method of claim 12, wherein the muscarinic antagonist is selected from a group consisting of; an atropine, a latrotoxin, a scopolamine, a propantheline, a pirezapine, and a derivative thereof.

14. The method of claim 1, wherein the agent is administered intravenously, intraperitonially, ophthalmologically, buccal, intracoronary, intramuscularly, topically, intranasally, rectally, sublingually, orally, subcutaneously, by patch, or inhalation.

15. The method of claim 1, wherein the subject is a human.

16. The method of claim 1, wherein the heart rate of said subject is compared to a population of aged-matched healthy individuals.

17. The method of claim 12, wherein the result of the administration of a muscarinic antagonist provides relief of a heart disorder in subjects who demonstrate a reduction in heart rate after administration of the cholinergic agent or a derivative thereof.

18. The method of claim 13, wherein the muscarinic antagonist is atropine.

* * * * *